United States Patent

Goldfain et al.

[11] Patent Number: 6,065,837
[45] Date of Patent: May 23, 2000

[54] OPHTHALMOSCOPE COMPRISING DEFOCUSED LIGHT SOURCE

[76] Inventors: Ervin Goldfain, 4422 Cleveland Rd., Syracuse, N.Y. 13215; William Lagerway, 7 Mandy Rue, Auburn, N.Y. 13021; Chris R. Roberts, 202 Tudor La.; Steven R. Slawson, 405 Oakridge Dr., both of Camillus, N.Y. 13031; Allan I. Krauter, 2224 W. Lake Rd., Skaneateles, N.Y. 13152

[21] Appl. No.: 09/198,545

[22] Filed: Nov. 24, 1998

[51] Int. Cl.⁷ .................................................. A61B 3/10
[52] U.S. Cl. ................................................ 351/205
[58] Field of Search ................................ 351/205, 206, 351/214, 215, 221, 246; 362/105

[56] References Cited

U.S. PATENT DOCUMENTS

| | | |
|---|---|---|
| 4,422,736 | 12/1983 | Nunokawa . |
| 4,439,024 | 3/1984 | Ito . |
| 5,255,025 | 10/1993 | Volk ........................................ 351/205 |
| 5,713,047 | 1/1998 | Kohayakawa . |
| 5,722,762 | 3/1998 | Soll ........................................ 362/105 |
| 5,751,395 | 5/1998 | Thall . |
| 5,880,813 | 3/1999 | Thall ...................................... 351/221 |

*Primary Examiner*—George Manuel
*Attorney, Agent, or Firm*—Wall, Marjama Bilinski & Burr

[57] ABSTRACT

The invention is an ophthalmoscope having an imaging path and imaging axis which includes a light source disposed in the imaging path at or in proximity with the imaging axis. Disposing the light source directly in the imaging path at or in proximity with the imaging axis provides numerous illumination and other operational advantages. When the light source is of sufficiently small size and is disposed in a sufficiently defocused position in relation to any retinal focal plane of the ophthalmoscope, the light source, for practical purposes, cannot be perceived by a user.

27 Claims, 5 Drawing Sheets

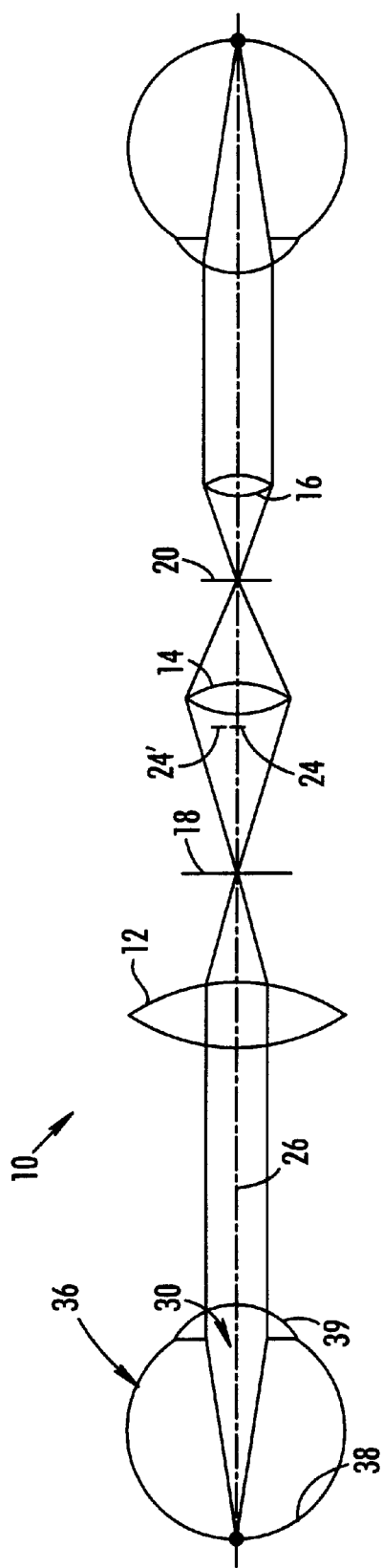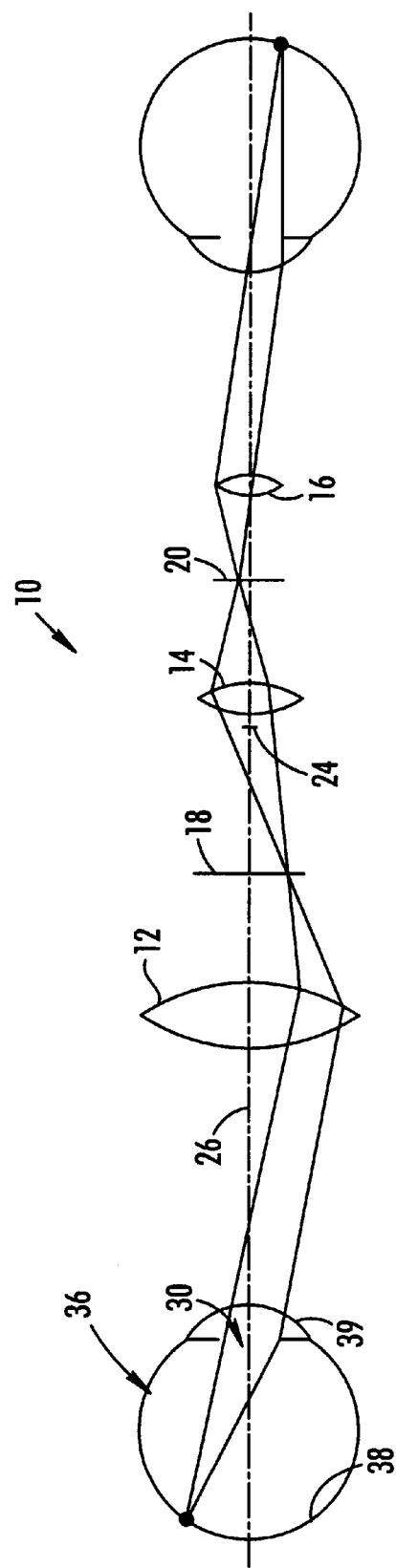
FIG. 1A
FIG. 1B

OPHTHALMOSCOPE COMPRISING DEFOCUSED LIGHT SOURCE

BACKGROUND OF THE INVENTION

1. Field of the Invention

This invention relates generally to medical diagnostic instruments, and specifically to an ophthalmoscope for use in retinal viewing.

2. Background of the Prior Art

Ophthalmoscopes for use in imaging a patient's retina include an optical imaging path for imaging a retina through a pupil and an illumination path for illumination of a retina by light rays entering an eye through a pupil.

A challenge inherent in designing such devices is that both the optical imaging path for imaging a retina and the optical illumination path for illuminating the retina are both ideally centered on the same axis, the optical axis of the pupil of an eye being viewed.

In general, there have been two approaches in response to this inherent challenge of ophthalmoscope design. A first approach, as in a traditional direct view ophthalmoscope, is to move the illumination pathway off axis slightly so that a retina can be directly viewed. Problems with this approach are that illumination light rays do not illuminate the same area being viewed, and that there is not appropriate space in an optical imaging path of such a system for a lens assembly which would expand a field of view.

A second approach to the inherent challenge mentioned above is to design an indirect ophthalmoscope which provides for larger field of view by disposing a partially transmitting illumination light source, such as a beam splitter, which allows receive optical light to pass therethrough, embodied for example in Model 11305 ophthalmoscope available from Reichert Ophthalmic. A major drawback with such a design is that the system is affected by significant light losses. An indirect ophthalmoscope embodying the beam splitter approach embodies a typical light loss of about 75% throughout the system. Because of the system light losses in such ophthalmoscopes, ophthalmoscopes embodying the beam splitter approach require high powered (e.g. above about 10 W) light sources in order to provide sufficient illumination of a retina. High power light sources, in general, are difficult to package, consume excessive amounts of input power, and produce large amounts of heat and unwanted light such as glare.

Cameras for retinal imaging, such as fundus cameras, provide high quality imaging, but are expensive, typically require pupil dilation for entry into an eye, and typically require operation control by a highly skilled and trained camera operator.

There is a need for a compact, lower power ophthalmoscope which provides sufficient retinal illumination and which facilitates wide field retinal imaging without requiring pupil dilation.

SUMMARY OF THE INVENTION

According to its major aspects and broadly stated the present invention is a compact, lower power ophthalmoscope which provides for wide field retinal imaging and ease of entry into nondilated eyes. The term "imaging" as used herein shall apply both to all-optical viewing systems and to optoelectronic image capture systems.

In a preferred embodiment, an ophthalmoscope according to the invention includes a light source disposed in the optical receive or optical imaging path at or in proximity with the imaging axis. The light source is particularly positioned and sized so that the light source disposed in the optical imaging path has minimal impact on the quality of a transmitted retinal image. Designed and positioned properly, the light source, for practical purposes, cannot be perceived by a user.

In order to minimize the impact of the light source on the quality of a transmitted image, the light source can be positioned so that the source is in a highly defocused position in relation to any image focal plane of the ophthalmoscope that is conjugate to a patient's retina in an operative position. In addition, the impact of the light source on the quality of an image can be reduced further by minimizing the size of the light source disposed in the imaging path.

The size of the light source is minimized in part simply by the selection of a light source which does not transmit light in the direction of imaging, such as a light reflecting light source, as the light source for illuminating a retina. Utilizing a light reflecting light source prevents light losses (inherent in the selection of a beam splitter as a light source), and allows a retina to be sufficiently illuminated with use of a light source which consumes a minimal amount of power. Disposing a fully reflecting light source in the optical imaging path facilitates tremendous gains in light transmission efficiency in comparison to a beam splitter ophthalmoscope design of the prior art. An ophthalmoscope designed in accordance with the present invention exhibits typical light losses in the approximate range of about 5% to 15% as compared to the light losses of about 75% in an ophthalmoscope including a beam splitter.

In one embodiment, the imaging path light source is provided by a small "spot" mirror which operates in association with a condenser lens and with a light-generating light source. In such an embodiment, the condenser lens converges light rays from the light-generating light source onto the spot mirror.

In a preferred illumination system of the invention, an objective lens converges light directed by the imaging path light source. Optimal illumination of a retina in such a system is provided when a cornea is positioned at the point of convergence of such light rays, which diverge inside an eye to illuminate a large surface area of a retina.

These and other details, advantages and benefits of the present invention will become apparent from the detailed description of the preferred embodiment hereinbelow.

BRIEF DESCRIPTION OF THE DRAWINGS

The preferred embodiment of the invention will now be described by way of example only, with reference to the accompanying figures wherein the elements bear like reference numerals, and wherein:

FIG. 1A is a functional schematic diagram of an ophthalmoscope according to the invention including on-axis receive path light rays illustrating operation of an optical receive imaging system;

FIG. 1B is a functional schematic diagram of an ophthalmoscope according to the invention including off-axis receive path light rays illustrating operation of an optical receive imaging system;

DETAILED DESCRIPTION OF THE INVENTION

Figure 2:
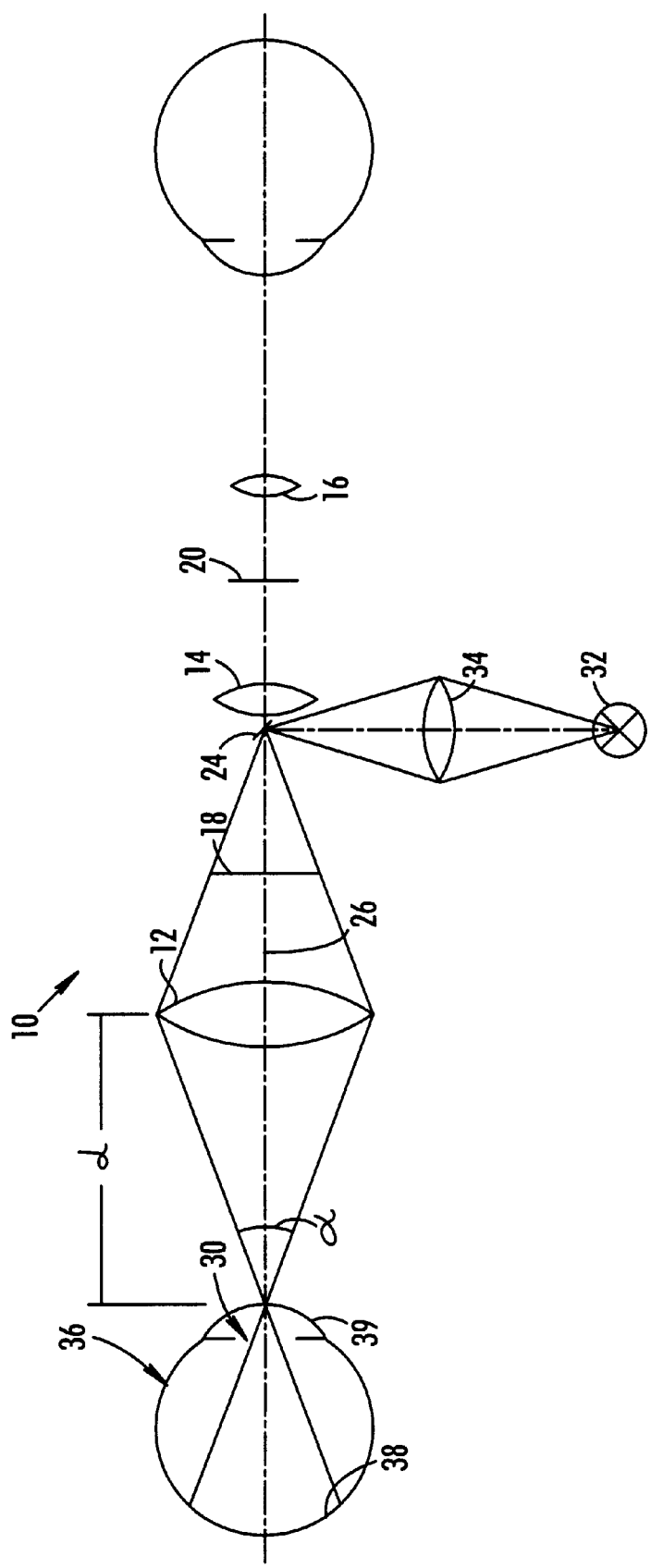
FIG. 2 is a functional schematic diagram of an ophthalmoscope according to the invention including illumination light rays illustrating operation of an illumination system.

A preferred ophthalmoscope according to the invention for use in illuminating and forming an image of a retina is described with reference to FIGS. 1A–1B and 2. FIGS. 1A and 1B show light rays in an optical receive imaging system while FIG. 2 shows light rays of an illumination system of an ophthalmoscope 10 according to the invention.

Referring first to aspects of an imaging system illustrated with reference to FIGS. 1A and 1B, an imaging system of a preferred embodiment of the invention includes objective lens 12 (which also forms part of the illumination system), imaging lens 14 and eyepiece lens 16. In all references herein, the term "lens" can refer to a single optical element or a plurality of elements functioning together. A retinal focal plane 18 is defined intermediate objective lens 12 and imaging lens 14, while an eyepiece focal plane 20 is defined intermediate imaging lens 14 and eyepiece lens 16.

An important aspect of the imaging system is that illumination source 24 is disposed in the receive optical path. In particular, source 24 is disposed at or in proximity with imaging axis 26, which during examination of a patient, is approximately coincident with the optical axis of a patient's pupil 30. Providing a source 24 in an optical receive path at or in proximity with imaging axis 26 enables improved illumination of a patient's retina. However, disposing a light blocking object in an optical receive path, by definition, also unavoidably blocks a certain amount of received light and thereby diminishes the ability of an imaging system to transmit an image to the retina.

Figure 3:
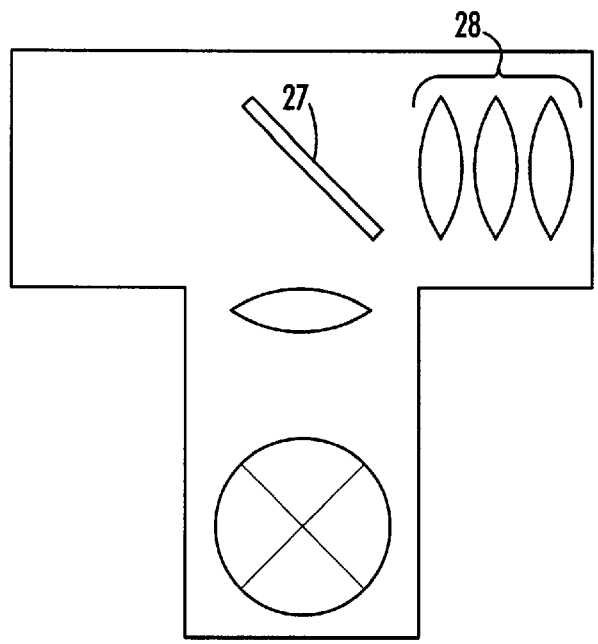
FIG. 3 is a functional schematic diagram of an ophthalmoscope according to a prior art design including a beam splitter for directing light toward a retina.

The traditional response to this light blocking problem is the solution provided in the prior art design of FIG. 3. In this design, a beam splitter 27 is disposed in the optical receive path which directs a percentage of light from a source to retina 38, and allows a percentage of light reflected from retina 38 to be transmitted to viewing lens system 28. A major limitation of this solution is that a relatively high powered light source (e.g. above about 10 W) is required to offset the losses of light due to inefficiencies of transmission through the beam splitter 27 in both the illumination and receive optical paths. High power light sources, in general, require a large amount of input power, pose packaging problems, produce excessive amounts of heat and unwanted light such as glare, and subject patients to an increased risk of potentially harmful light rays.

The inventors of the present invention propose a solution to the light blocking problem that is different from those involving a beam splitter. The inventors found that by appropriate positioning and sizing of a light source, that either a light-generating or light reflecting light source could be disposed directly in an optical receive path in such a way that all of the illumination benefits of such positioning are realized without seriously diminishing the capacity of the system to transmit an image of a retina. By utilizing a light source that does not transmit light in the direction of the optical imaging path the light loss problem inherent in the beam splitter solution of the prior art design is avoided. It was found that utilizing a light source that does not transmit light in the direction of the optical imaging path provides a series of benefits which are described hereinbelow.

Most importantly, because light-losses are eliminated, a smaller, more concentrated point-like light source can be utilized to completely illuminate a retina. A point-like light source consumes less space and less input power than a light source required in the prior art. A point-like light source, it will be seen, also improves the illumination capability of the ophthalmoscope since a point-like light source facilitates satisfactory illumination of a retina by reducing glare via point-like illumination of a patient's cornea.

To the end that light source 24 in FIGS. 1A–2 has a minimal impact on the imaging system's transmission of a retinal image, there are essentially two important considerations to be made in designing a light source for use in an ophthalmoscope according to the invention. The first consideration involves the positioning of source 24 while the second involves the size of source 24.

With reference to the positioning consideration, source 24 should be positioned in a highly defocused position in relation to any image plane of the ophthalmoscope conjugate to a patient's retina in an operative position. As shown in the imaging system diagram of FIGS. 1A and 1B, a highly defocused position for source 24 in relation to an imaging focal plane conjugate to a retina is provided by disposing source 24, intermediate retinal focal plane 18 and imaging lens 14. In general, source 24 becomes less in focus at any plane conjugate to and including the eyepiece focal plane 20 as the source is moved toward imaging lens 14 and away from retinal focal plane 18. Preferably, source 24 is positioned as close as is physically possible to lens 14.

With reference to the size consideration of source 24, the negative impact of source 24 on image transmission is minimized by decreasing the dimensions of source 24 perpendicular to axis 26. The dimensions of source 24 perpendicular to imaging axis 26 can be reduced by a certain design for source 24. In theory, a workable but less than optimally performing embodiment of the invention could be provided by disposing a pointlike light-generating light source, such as a filament based lamp, an arc lamp, a fiber optic light source or a solid state light source directly in the receive optical path at the location of source 24 shown in FIGS. 1A and 1B.

With presently available technology, light sources are sufficiently large that they block a substantial amount of light in the optical receive path resulting in reduced image quality. Therefore a preferred light source for the ophthalmoscope of FIGS. 1A and 1B is the light source described with reference to FIG. 2. In the embodiment of FIG. 2, light source 24 is provided by a reflective element such as a mirror, which operates in association with a light-generating light source 32 and a condenser lens 34 which converges light from source 32 onto mirror 24. Mirror 24 should be sized no larger than is necessary to receive and reflect substantially all light collected from light generating light source 32. To the end that the dimensions of mirror 24 perpendicular to axis 26 are minimized, condenser lens 34 can operate to converge light rays originating from source 32 onto a point at about a center of mirror 24. Light generating light source 32 is preferably a small point-like light source. In one particular embodiment of the invention, light generating light source 32 is provided by a miniature gas filled incandescent lamp.

Continuing with reference to FIG. 2, further aspects of the illumination system are described in detail. Objective lens 12 which forms part of imaging system also forms part of the illumination system. A patient's eye is positioned such that it is optimally illuminated by the illumination system when light transmitted by objective lens 12 converges at cornea 39 and diverges inside eye 36 to illuminate a wide area of retina 38 as shown. In this way, objective lens 12 enables a large amount of light to enter a small pupil 30 having a diameter as small as 2 mm.

In a specific example of an ophthalmoscope designed according to the general configuration described with reference to FIGS. 1A–2, the objective lens 12 may be provided by a lens system having a focal length of about 25 mm, and a back focal length of about one-half the focal length. The ophthalmoscope may be configured so that the objective lens system is positioned about 25 mm from a patient's cornea when in an operative position. The objective lens system accepts parallel or nearly parallel light from a patient's eye and focuses the light to an internal image located at or near the back focal plane 18 of the objective. The objective lens system may have a diameter of about 25 mm. Imaging lens 14, meanwhile, may be provided by a lens system having a focal length of about 25 mm, a back focal length of about 18 mm and a clear aperture of about 20 mm. The imaging lens may project an internal image from the objective focal plane 18 to eyepiece focal plane 20 at a magnification of about 0.6×. Eyepiece focal plane 20 may have an aperture of about 8 mm in diameter, corresponding to the focal plane diameter of a typical 20× eyepiece. The axial length from objective lens 12 to eyepiece focal plane 20 may be about 160 mm. In the illumination system described with reference to FIG. 2, condenser lens 34 may be provided by a condenser system having a numerical aperture of about 0.2 to 0.4, working at a magnification of about 1× to 2×, with a focal length of about 9 mm.

Figure 4:
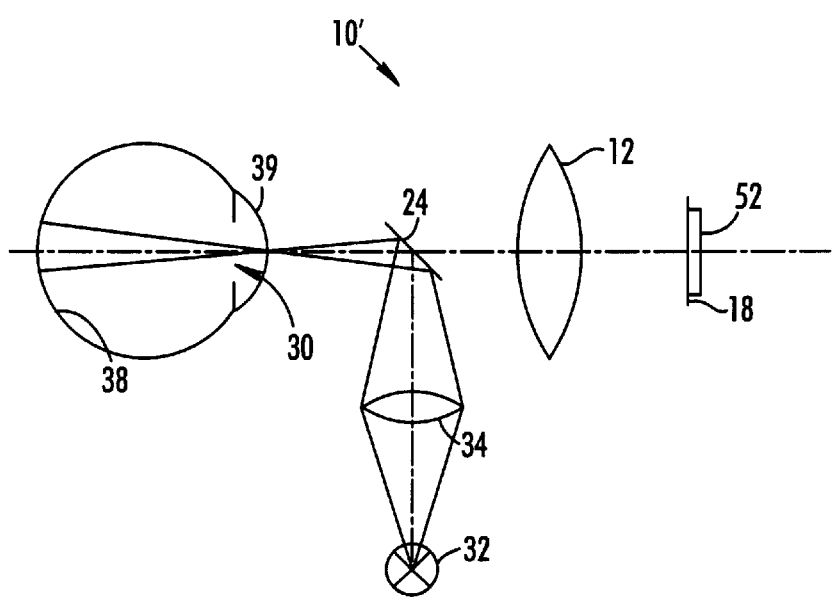
FIG. 4 is a functional schematic diagram illustrating operation of an alternative embodiment of an ophthalmoscope according to the invention.

An alternative optical configuration for an ophthalmoscope 10' according to the invention is described with reference to FIG. 4. In the ophthalmoscope of FIG. 4, light source 24 is disposed forward of objective lens 12 and imaging lens 14 is deleted. Light source 24 is disposed in a highly defocused position in relation to retinal focal plane 18 by disposing light source 24 in proximity with objective lens 12. In the embodiment of FIG. 4, objective lens 12 does not form part of the optical illumination system. Instead, illumination light rays which converge at a cornea 39 and diverge toward a retina 38 are formed by disposing condenser lens 34 in relationship with light source mirror 24 such that light rays reflected from the mirror converge after being reflected. Further with reference to the embodiment of FIG. 4, eyepiece lens 16 is deleted and replaced with image sensor 52, such as a CCD image sensor, which is positioned on retinal focal plane 18. A processor system (not shown) in communication with sensor 52, can be configured to capture image signals generated by sensor 52, process such signals, and if desirable, electronically reverse or magnify any captured images to accomplish the function provided optically by imaging lens 14 of the ophthalmoscope of FIGS. 1A–2.

The conventional lenses in the systems described hereinabove can be replaced with similarly functioning optical elements such as diffractive lenses, binary gratings, phase filters, holographic optical elements (HOE), gradient-index lenses, and hybrid optical elements.

Some basic working embodiments of the invention having been described, certain additional features which may be incorporated in the invention will now be described in detail.

Figure 5:
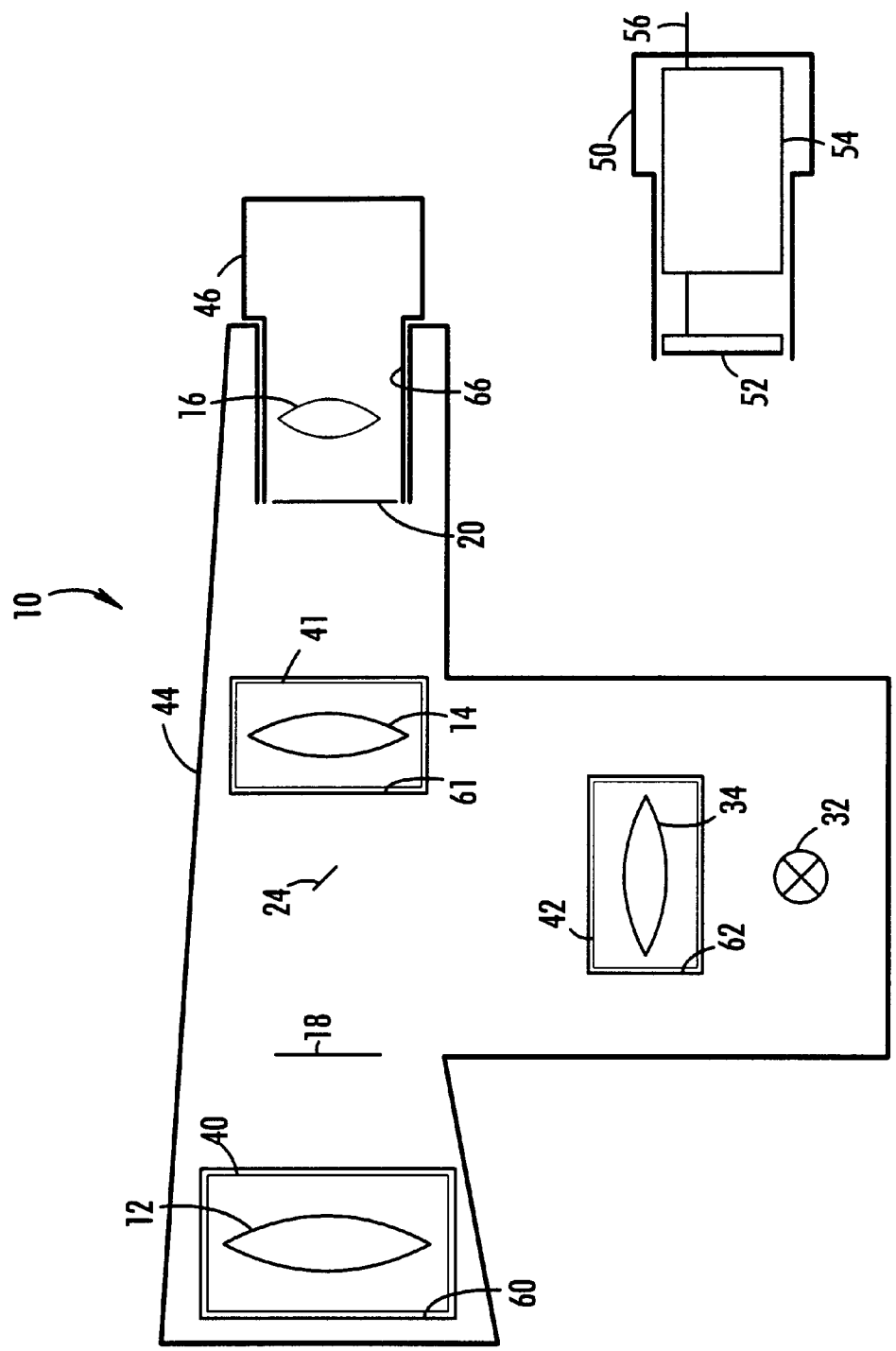
FIG. 5 is a physical schematic diagram illustrating a possible physical embodiment of the invention.

Shown in FIG. 5 is a physical schematic diagram of an embodiment of the invention which can be reconfigured for optimizing various functional aspects of the ophthalmoscope. In the embodiment of FIG. 5, housing 44 of ophthalmoscope 10 includes holders 60, 61, 62 and 66 and replaceable lens modules 40, 41, 42 and 46 replaceably received in their respective holders. As will be explained hereinbelow, replacing a certain lens module or a grouping of lens modules changes functional aspects of the ophthalmoscope enabling the ophthalmoscope to be optimized for a specific intended use.

For example, with reference to FIGS. 1A–2, it is seen that the area of retina that is illuminated by the illumination system depends on the diameter and optical power of objective lens 12 and on the magnification selected for the lens at the operative position of the ophthalmoscope. This area corresponds to the angle a as shown in FIG. 2. The field of view of the imaging system, meanwhile, also depends on the diameter and optical power of objective lens 12 and on the magnification selected for the lens at the operative position of the ophthalmoscope. In the particular embodiment of FIGS. 1A–2, the field of view of the imaging system and the angle of illumination, α, desirably correspond to one another.

It is desirable that the ophthalmoscope 10 images a wide field of view. While a wide field of view and illumination angle, α, are highly desirable for an accurate and efficient diagnosis of various problems, a smaller field of view and illumination angle are desirable for ease of use. As the angle of illumination, α, becomes less steep, illumination light rays are more easily directed into an eye through a pupil, so that entry into an eye is easier. This is because as the illumination angle, α, becomes less steep, light rays from source 24 can be directed through pupil 30 over a greater range of cornea to lens distances, d of FIG. 2. Accordingly, in view of the above, it would be beneficial to provide an ophthalmoscope which could be configured either for optimized field of view or optimized ease of use.

A possible embodiment of reconfigurable ophthalmoscope according to the invention is described with reference to the physical schematic diagram of FIG. 5. This particular physical layout diagram includes first and second lens modules 40 and 41. First lens module 40 includes objective lens 12, while second lens module 41 includes imaging lens 14. While the field of view and illumination angle depend mainly on the sizing, optical power, and magnification selected for objective lens 12, imaging lens 14 will normally be replaced along with lens 12, since the sizing and optical power of lens 14 are coordinated with lens 12. The housing 44 and lens modules 40, 41 are complementarily designed so that the modular lens modules can be manually removed and replaced from housing 44 while maintaining a common eyepiece focal plane 20. In a reconfigurable ophthalmoscope, a first set of lens modules can be provided to configure the ophthalmoscope for imaging a wide field of view, while a second set of modules can provide a reduced field of view (but with increased magnification), making the instrument easier to maneuver into an operative position. Such an ophthalmoscope can be made easier to use simply by replacing the first set of lens modules with the second set of lens modules.

To complement the change in field of view accomplished by changing the first and second lens modules, the illumination condenser system may also be changed in a modular fashion to optimize the illumination characteristics to suit the user's needs. In all condenser systems with a given condenser size, the ability to collect the light from a light generating light source is balanced with the angle at which the light can be transmitted and the magnification at which the image of the light generating light source is projected. An increase in light collection corresponds to an increase in the collection angle and an increased magnification. The lenses inside the illumination lens module 42 can be selected such that the illumination system matches the numerical aperture of the given objective module 40.

A number of features may be incorporated in the present invention which operate to reduce glare. In general, glare is produced in an ophthalmoscope when light rays not forming an image of retina 38 are reflected back to focal plane 20.

Glare is produced, for example when light rays from a light source impinge on the highly reflective cornea 39. Such a source for glare is prevalent in may types of prior art ophthalmoscopes which "flood" a cornea with bright light sources or which direct light toward a retina with use of a collimating lens. In the present invention, this type of glare, known as patient corneal glare, may be substantially reduced by the use of a converging lens, such as lens 12 for directing light toward a patient's retina in combination with a small point-like light source as has been described herein. In the present invention, glare is reduced since a patient's retina is completely and efficiently illuminated with a minimal amount of light from a point-like light source.

Corneal glare in the present invention can be reduced further by positioning light source 24 in the optical receive path so that source 24 is conjugate to the surface of cornea 39. In this way, many light rays which do happen to be reflected from cornea 39 are imaged directly onto light source 24. If primary light source 24 is provided by a mirror as shown, these light rays corresponding to a cornea image are directed away from eyepiece focal plane 20, blocking corneal glare.

Other sources of glare can be reduced by additional enhancements of the invention. For example, in the embodiment of FIGS. 1A–2 the light source can be positioned in a slightly shifted location relative to imaging axis 26, as is indicated by light source 24' in FIG. 1A, to help suppress both the internal and corneal glare. In addition, polarizers can be disposed in the illumination and imaging paths to further reduce corneal glare.

While the advantages of providing a light reflecting or light-generating light source in the optical receive path have been described herein, it may be desirable in certain instances to sacrifice the illumination benefits of a reflecting or light-generating source in the interest of further reducing the impact of source 24 on the imaging system. In such embodiments, a reflecting or light-generating light source can be replaced with similar sources which transmit light such as a light pipe, a light guide, a diffractive optical element or a holographic optical element (such as periodic gratings on planar or curved substrates or diffractive homogenizers).

Figure 6:
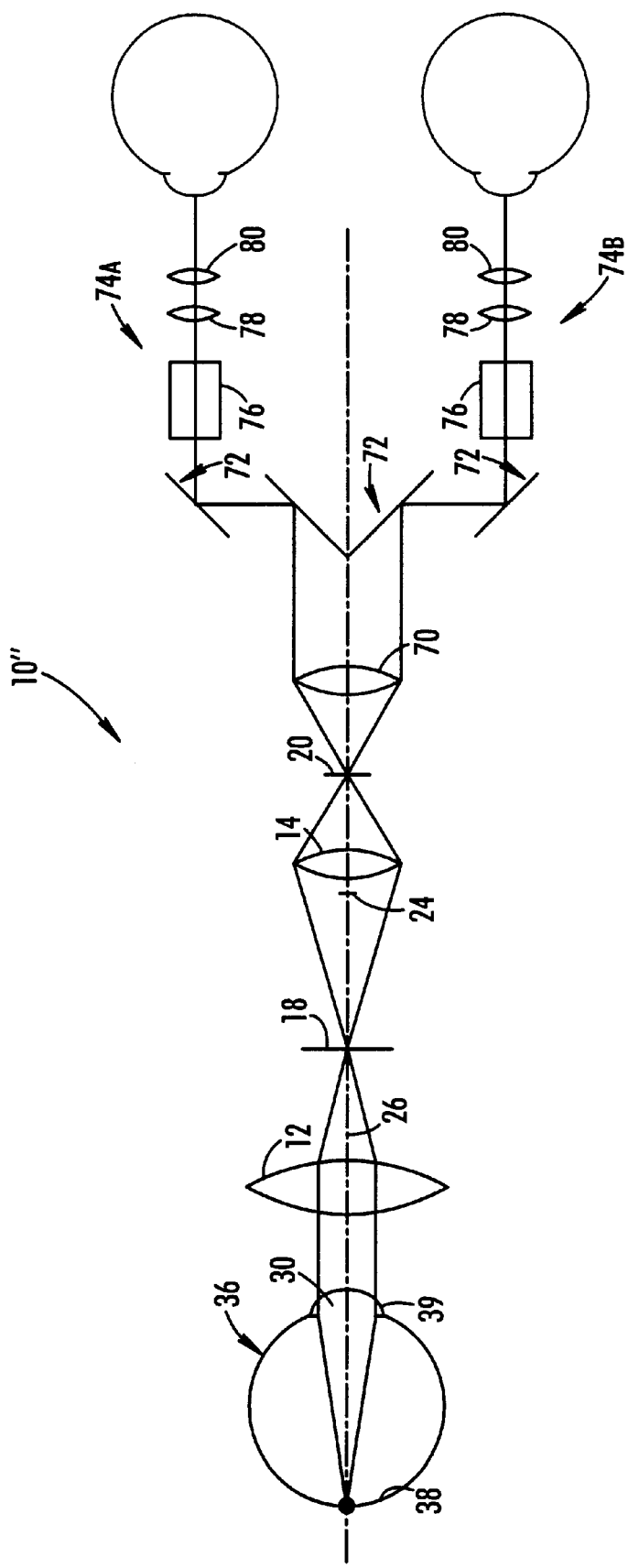
FIG. 6 is a functional schematic diagram illustrating operation of an embodiment of the invention adapted for stereoscopic viewing.

In an alternative embodiment of the invention, the invention can be adapted to provide stereoscopic viewing. An embodiment of an ophthalmoscope 10" adapted to provide stereoscopic viewing is shown in FIG. 6. As seen in FIG. 6, a stereoscopic ophthalmoscope according to the invention typically includes a collimating optical element 70 for collimating light rays of the imaging path, and separating optics 72 for splitting light rays transmitted by collimating optics 70 into two separate imaging paths 74A and 74B. Separating optics 72 typically include a combination of such optical elements as prisms and/or mirrors. Continuing with reference to FIG. 6, stereoscopic ophthalmoscope 10" may further include orientation optics 76 disposed in each stereoscopic imaging path 74A, 74B for setting the orientation of images transmitted by separating optics as is necessary. Orientation optics 76 may include such optical elements as prism and/or mirror optical elements. Stereoscopic ophthalmoscope 10" may further include decollimation optics 78 and eyepiece optics 80 disposed in each imaging path 74A and 74B. Each eyepiece optics 80 recollimates light so that images can be perceived by a viewer. The eye tubes (not shown) of eyepiece optics 80 may be arranged in an orientation slightly diverging toward a viewer's eyes to approximate the direct viewing condition of a target by a pair of eyes.

In a further alternate embodiment, the invention can be adapted to capture electronic images representing an imaged retina. One such embodiment has been described with reference to FIG. 5. In FIG. 5, an ophthalmoscope 10 is shown that can be reconfigured for electronic image capture. FIG. 5 shows an ophthalmoscope adapted so that eyepiece module 46 can be replaced with a video module 50. It is seen that ophthalmoscope 10 normally includes an eyepiece module 46 having an eyepiece lens 16 which collimates imaging light rays so that a retinal image can be viewed by user. Eyepiece 46 can be replaced with video module 50 which includes certain components that configure the ophthalmoscope for video capture. In particular, a video module 50 may contain an image sensor 52, such as a CCD image sensor, which is in an operative position in relation to the imaging system when the video module is installed in holder 66. The image sensor 52 is in electrical communication with a processor system 54 which may be programmed to control image sensor 52 and to capture and, possibly, store image data generated by and received from image sensor 52. While processor system 54 is shown as being disposed in video module 50, it is understood that processor system 54 could be disposed external to video module 50. The video module 50 may further be in communication with an external display screen and/or an external processing system via cable 56, for example, so that video images captured by image sensor can be displayed or otherwise output, and possibly archived.

Video module 50 is designed so that image sensor 52 lies on eyepiece focal plane 20 when module 50 is in an operative position in holder 66. It is seen that an ophthalmoscope of the invention can be configured for video capture by replacing eyepiece module 46 with a video module 50 without adding or replacing additional lenses of the imaging system.

While the present invention has been particularly shown and described with reference to the preferred mode as illustrated in the drawings, it will be understood by one skilled in the art that various changes in detail may be effected therein without departing from the spirit and scope of the invention as defined by the claims.

What is claimed is:

1. An eye viewing device for use in viewing a structure of an eye, said ophthalmoscope comprising:
   a patient end and a viewing end;
   an imaging system having an imaging path and at least one retinal image focal plane; and
   an illumination system including a light source disposed in said imaging path and positioned in a defocused position in relation to said at least one retinal image focal plane wherein said illumination system is adapted to generate illumination light rays that converge substantially at or forward of said patient end, whereby said converged light rays can easily enter a pupil arranged forward of said patient end.

2. The eye viewing device of claim 1, wherein said light source comprises a reflective element.

3. The eye viewing device of claim 1, wherein said light source comprises a light-generating light source.

4. The eye viewing device of claim 3 wherein said light source is provided by a miniature incandescent lamp.

5. The eye viewing device of claim 1, wherein said illumination system comprises:
   a reflective element defining said light source;
   a light-generating light source directing light toward said reflective element; and
   a condenser optical element interposed between said light-generating light source and said reflective element, said condenser optical element converging light rays from said light-generating light source onto said reflective element.

6. The eye viewing device of claim 5, wherein said light-generating light source is provided by a miniature incandescent lamp.

7. The eye viewing device of claim 1, wherein said imaging system includes an objective optical element and an imaging optical element, and wherein said light source is disposed intermediate said objective optical element and said imaging optical element.

8. The eye viewing device of claim 7, wherein said light source is disposed in close proximity with said imaging optical element.

9. The eye viewing device of claim 7, wherein said eye viewing device includes a housing, and wherein at least one of said objective optical element and said imaging optical element are adapted to be replaceably disposed in said housing.

10. The eye viewing device of claim 1, wherein said light source is a light transmitting light source selected from the group consisting of a light pipe, a light guide, a diffractive optical element and a holographic optical element.

11. The eye viewing device of claim 1, wherein said imaging system includes an image sensor for generating electrical signals representing said retina.

12. The eye viewing device of claim 1, wherein said imaging system includes an imaging axis, and wherein said light source is disposed slightly off said imaging axis.

13. The eye viewing device of claim 1, wherein said eye viewing device comprises stereoscopic optics for forming a stereoscopic image of said eye structure.

14. The eye viewing device of claim 13, wherein said stereoscopic optics include:
   collimating optics for collimating light along said imaging path;
   separating optics for separating light transmitted by said collimating optics along first and second light paths;
   orientation optics disposed in at least one of said first and second paths for setting an orientation of received images;
   decollimating optics disposed in at least one of said first and second optical paths for decollimating light transmitted by said adjusting optics; and
   eyepiece optics disposed in at least one of said first and second paths for recollimating light decollimated by said decollimating optics.

15. The eye viewing device of claim 1, wherein said light source is disposed in a position that is substantially conjugate with a patient's cornea when said device is in an operative position in relation to said eye.

16. An eye viewing device comprising:
   a housing having an eyepiece holder;
   an eyepiece having an eyepiece lens, said eyepiece being adapted to be received in said eyepiece holder; and
   a video module having an image sensor, said video module being adapted to be received in said eyepiece holder wherein said eyepiece holder is adapted to receive only one of said eyepiece or said video module at a given time.

17. The eye viewing device of claim 16, further comprising an imaging system including a image focal plane disposed in said housing, and wherein said video module is configured so that said image sensor lies substantially on said image focal plane when said video module is received in said holder.

18. An eye viewing device for use in viewing a structure of an eye, said device including:
   a patient end and a viewing end;
   an imaging system having an imaging path and at least one retinal image focal plane; and
   an illumination system including a light source disposed in said imaging path and positioned in a defocused position in relation to said retinal image focal plane, said illumination system including an objective lens disposed intermediate said light source and said patient end, said light source positioned beyond said retinal image focal plane in a direction away from said objective lens so that said objective lens operates to converge illumination light rays generated by said light source.

19. The eye viewing device of claim 18, wherein said illumination system comprises:
   a reflective element defining said light source;
   a light-generating light source directing light toward said reflective element; and
   a condenser optical element interposed between said light-generating light source and said reflective element, said condenser optical element converging light rays from said light-generating light source onto said reflective element.

20. The eye viewing device of claim 18, wherein said imaging system includes an image sensor for generating electrical signals representing said structure.

21. The eye viewing device of claim 18, wherein said device comprises stereoscopic optics for forming a stereoscopic image of said eye structure.

22. The eye viewing device of claim 18, wherein said light source is disposed in a position that is substantially conjugate with patient's cornea when said device is in an operative position in relation to said eye, so that light rays reflected from said cornea are converged onto said light source.

23. An eye viewing device for use in viewing a structure of an eye, said device including:
   a patient end and a viewing end;
   an imaging system having an imaging path and at least one retinal image focal plane; and
   an illumination system including a light source disposed in said imaging path in a position that is defocused in relation to said at least one retinal image focal plane and that is substantially conjugate to a patient cornea when said device is in an operative position in relation to said eye, so that light rays reflected from said cornea are converged onto said light source.

24. The eye viewing device of claim 23, wherein said illumination system comprises:
   a reflective element defining said light source;
   a light-generating light source directing light toward said reflective element; and a condenser optical element interposed between said light-generating light source and said reflective element, said condenser optical element converging light rays from said light-generating light source onto said reflective element.

25. The eye viewing device of claim 23, wherein said imaging system includes an image sensor for generating electrical signals representing said structure.

26. The eye viewing device of claim 23, wherein said device comprises stereoscopic optics for forming a stereoscopic image of said eye structure.

27. An eye viewing device comprising:

a housing;

an imaging system;

an illumination system;

an objective lens holder for receiving an objective lens module;

an imaging lens holder for receiving an imaging lens module;

a first objective lens module and imaging lens module pair configured to provide wide field viewing; and a second objective lens module and imaging lens module pair configured to provide narrower field viewing and easier entry than said first objective lens module and imaging lens module pair, wherein said objective lens and imaging lens holders are adapted to receive only one of said first or second objective lens and imaging lens modules at a given time.

\* \* \* \* \*

UNITED STATES PATENT AND TRADEMARK OFFICE
CERTIFICATE OF CORRECTION

PATENT NO. : 6,065,837
DATED : May 23, 2000
INVENTOR(S) : Ervin Goldfain, William Lagerway, Chris R. Roberts, Steven R. Slawson and Allen I. Krauter It is certified that error appears in the above-identified patent and that said Letters Patent is hereby corrected as shown below:

Title page insert:

--[73] Assignee: Welch Allyn, Inc.
4314 State Street Road
Skaneateles, NY 13153 --.

Signed and Sealed this

Fifteenth Day of August, 2000

Attest:

Q. TODD DICKINSON

Attesting Officer

Director of Patents and Trademarks